(12) United States Patent
Wilson et al.

(10) Patent No.: US 7,621,944 B2
(45) Date of Patent: *Nov. 24, 2009

(54) THERMAL PACK

(75) Inventors: Jeffrey A. Wilson, Cleveland Heights, OH (US); Jonathan W. Flick, Mentor, OH (US)

(73) Assignee: Wendell-Alan, Ltd., Cleveland, OH (US)

( * ) Notice: Subject to any disclaimer, the term of this patent is extended or adjusted under 35 U.S.C. 154(b) by 826 days.

This patent is subject to a terminal disclaimer.

(21) Appl. No.: 11/161,483

(22) Filed: Aug. 4, 2005

(65) Prior Publication Data

US 2006/0004427 A1 Jan. 5, 2006

Related U.S. Application Data

(63) Continuation-in-part of application No. 10/298,453, filed on Nov. 18, 2002, now Pat. No. 7,060,086.

(51) Int. Cl.
*A61F 7/00* (2006.01)

(52) U.S. Cl. .......................... 607/108; 607/114; 602/63

(58) Field of Classification Search ......... 607/108–112, 607/114, 96; 602/63
See application file for complete search history.

(56) References Cited

U.S. PATENT DOCUMENTS

| | | | | |
|---|---|---|---|---|
| 2,943,859 A | * | 7/1960 | William et al. | 473/214 |
| 3,631,854 A | * | 1/1972 | Fryer | 602/8 |
| 3,739,829 A | * | 6/1973 | Powell et al. | 152/521 |
| 3,934,583 A | | 1/1976 | Hollingshead et al. | |
| 3,978,531 A | * | 9/1976 | Ilon | 5/81.1 T |
| 4,228,792 A | * | 10/1980 | Rhys-Davies | 601/19 |
| 4,261,655 A | * | 4/1981 | Honigsbaum | 351/41 |
| 4,566,436 A | * | 1/1986 | Loefqvist | 128/898 |
| 4,868,967 A | * | 9/1989 | Holt et al. | 29/450 |
| 4,910,978 A | | 3/1990 | Gordon et al. | |
| 5,045,070 A | * | 9/1991 | Grodecki et al. | 604/271 |
| 5,052,387 A | * | 10/1991 | Natali | 607/108 |
| 5,070,597 A | * | 12/1991 | Holt et al. | 29/887 |
| 5,129,391 A | * | 7/1992 | Brodsky et al. | 607/110 |
| RE34,661 E | | 7/1994 | Grimm | |
| 5,342,385 A | * | 8/1994 | Norelli et al. | 606/193 |

(Continued)

FOREIGN PATENT DOCUMENTS

EP 1038510 9/2000

OTHER PUBLICATIONS

Pufferbelly Toys web page (undated) depicting and describing "water snake" novelty toy available from Toysmith, Inc.

*Primary Examiner*—John P Leubecker
(74) *Attorney, Agent, or Firm*—Rankin, Hill & Clark LLP (57) ABSTRACT

A thermal pack that includes a tubular body having a first opening, a second opening, an inner surface and an outer surface. The first opening, the inner surface and the second opening cooperate to define a passage through the tubular body for the limb. The inner surface and the outer surface of the tubular body are defined by a continuous eversion-limitless film of flexible material. A temperature-retaining fluid such as a water-based gel is received between the inner surface and the outer surface. The thermal pack can be positioned at a desired location on a limb by rolling the thermal pack onto the limb.

16 Claims, 9 Drawing Sheets

U.S. PATENT DOCUMENTS

| | | |
|---|---|---|
| 5,356,426 A | 10/1994 | Delk et al. |
| 5,389,065 A | 2/1995 | Johnson, Jr. |
| 5,411,541 A | 5/1995 | Bell et al. |
| RE35,113 E | 12/1995 | Grimm |
| 5,486,206 A | 1/1996 | Avery |
| 5,843,145 A | 12/1998 | Brink |
| 5,964,781 A * | 10/1999 | Mollenauer et al. ......... 606/213 |
| 6,082,025 A * | 7/2000 | Bonk et al. .................... 36/29 |
| 6,401,247 B1 | 6/2002 | Williams, IV |
| D464,140 S | 10/2002 | Lavin, Jr. |
| 6,623,426 B2 | 9/2003 | Bonadio et al. |
| 7,056,335 B2 * | 6/2006 | Agarwal et al. ............. 607/104 |
| 2002/0103520 A1 | 8/2002 | Latham |
| 2003/0135171 A1 | 7/2003 | Ingram et al. |

\* cited by examiner

THERMAL PACK

CROSS-REFERENCE TO RELATED APPLICATION

This application is a continuation-in-part of application Ser. No. 10/298,453, filed Nov. 18, 2002, now U.S. Pat. No. 7,060,086

BACKGROUND OF THE INVENTION

1. Field of Invention

The present invention relates to a thermal pack, and more particularly, to a thermal pack that can be positioned on a user's limb to provide circumferential thermal treatment at a desired location on the limb.

2. Description of Related Art

The generally accepted first aid treatment for strains, sprains, contusions, dislocations, uncomplicated fractures and other non-acute injuries to human limbs is often referred to by the acronym RICE, which stands for rest, ice, compression and elevation. Rest is prescribed because continued activity can cause further injury to the limb thereby delaying the healing process, increasing pain, and stimulating internal bleeding. Ice is prescribed because blood vessels contract when exposed to cold temperatures, which helps reduce swelling in the injured limb and also helps to reduce the extent of internal bleeding from injured capillaries and blood vessels. Compression is prescribed because it tends to hasten healing time by reducing swelling around injury. And, elevation of the limb above the heart is prescribed because it tends to reduce swelling in the limb and also tends to reduce pain.

Although ice is prescribed to treat injured limbs, ice can cause discomfort when placed between a compressive wrap and an injured limb because it is a rigid non-conforming solid. Ice is also difficult to position on an injured limb, and it tends to melt quickly, which results in a loss of the desired cold treatment and/or frequent disturbance of the injured limb to apply more ice. In view of these and other disadvantages, temperature-retaining gel-filled thermal packs are frequently used instead of ice in the first aid treatment of injured limbs. The gels used in such packs tend to remain cold for a longer period of time than ice, and such gels also preferably remain viscous at low temperatures, which allow them to more comfortably conform to the contours of the injured limb when placed between a compressive wrap and the injured limb.

Conventional gel-filled thermal treatment packs generally consist of a substantially flat flexible envelope that has been filled with a temperature-retaining gel material. Pre-chilled "flat packs" of this type are typically pressed into contact with an injured limb and over-wrapped with a suitable material such as an elastic bandage to hold it in place and provide compression to the injured limb. Some gel-filled thermal treatment packs are provided with straps or other means of securing the flat pack in contact with the injured limb.

Flat packs, while widely used to provide first aid treatment to injured limbs, present certain problems and disadvantages. One problem with flat packs is that they do not provide circumferential thermal treatment to injured limbs (i.e., thermal treatment completely surrounding the injured limb at the location of the injury). Flat packs are effective in applying cold treatment to injured limbs only insofar as they can be placed into contact with the injured limb. Thus, in order to provide circumferential or radial thermal treatment to an injured limb, it is typically necessary to apply more than one flat pack to the injured limb, which can present placement and retention problems. In addition, it is sometimes very difficult and time consuming to secure flat packs to an injured limb, even when the flat pack is provided with straps or other securing means.

BRIEF SUMMARY OF THE INVENTION

The present invention provides a thermal pack that can be positioned onto a user's limb to provide circumferential thermal treatment. A thermal pack in accordance with the invention comprises a tubular body having a first opening, a second opening, an inner surface and an outer surface. The first opening, the inner surface and the second opening cooperate to define a passage through the tubular body for the limb. The inner surface and the outer surface of the tubular body are defined by a continuous film of flexible material such as, for example, a copolymer of polyester and polyurethane. A temperature-retaining fluid such as a water-based gel is received between the inner surface and the outer surface. Optionally, a selectively pressurizable radial air bladder is formed on the outer surface of the tubular body. When inflated, the air bladder provides circumferential compression and support for the limb. An insulating layer (e.g., a fabric wrap) can be disposed between the inner surface of the thermal pack and the user's limb to protect the user's skin from frostbite.

The present invention also provides a method of treating an injured limb. The method according to the invention comprises providing a thermal pack in accordance with the invention, inserting the injured limb into the passage through the tubular body of the thermal pack, and positioning the thermal pack on the limb at a location where circumferential thermal treatment is desired. The diameter of the passage through the thermal pack can be smaller than, equal to or larger than the diameter of the injured limb. When the diameter of the passage through the thermal pack is smaller than the diameter of the injured limb, the inner surface of the tubular body to makes contact with the limb or an insulating layer disposed between the inner surface of the tubular body and the limb, causing the continuous film of flexible material to evert about the tubular body as the thermal pack is rolled up the limb. The continuous film of flexible material can be everted about the tubular body as many times or cycles as is needed to position the thermal pack on the desired portion of the limb. The tubular body gently conforms to the contours of the limb and provides even compression to the limb, but does not slide relative to the surface of the limb. When the diameter of the passage through the thermal pack is larger than the diameter of the limb, the thermal pack simply slips over the limb. The optional radial air bladder can be inflated to provide compression for the limb and also to insure that the inner surface of the thermal pack is positioned circumferentially into contact with the limb or an insulating layer disposed between the limb and the inner surface of the thermal pack.

As noted, a thermal pack according to the invention can be positioned at the desired location on a limb simply by rolling the thermal pack onto the limb. During rolling, the continuous film of flexible material engages the surface of the limb in a gentle compressive manner, but does not slide relative to the surface limb as the thermal pack is rolled onto the limb. The continuous film of flexible material stretches and conforms to the shape of the limb, providing compressive force and circumferential thermal treatment at the desired location. The thermal pack according to the invention can be retained in the desired location on the injured limb without the need for additional securing means or over-wrapping, and thus can be quickly and easily installed by a user using one hand. This allows for easy self-treatment of injured limbs.

The present invention also provides a method of manufacturing a thermal pack. The method of manufacturing a thermal pack according to the invention comprises: forming a film of flexible material into a tube having a first edge defining a first open end and an opposing second edge defining a second open end; folding the tube such that the first edge and the second edge are concentric to each other; and sealing the first edge to the second edge to form a tubular body having a first opening, a second opening, an inner surface and an outer surface, wherein the first opening, the inner surface and the second opening cooperate to define a passage through the tubular body for a limb. A temperature-retaining fluid and optionally an insert are disposed into a space between the inner surface and the outer surface before or after the first edge and the second edge are sealed to form the tubular body.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
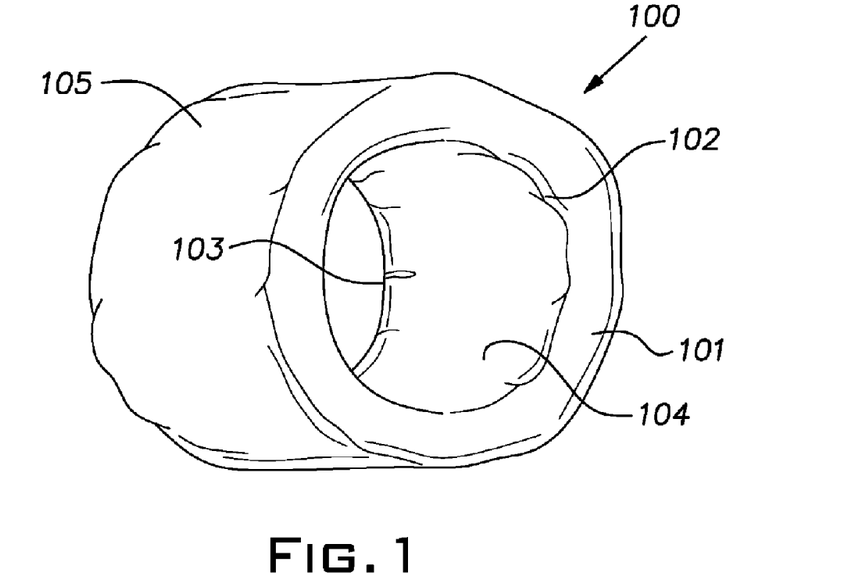
FIG. 1 is a perspective view of an exemplary embodiment of a thermal pack according to the invention.
Figure 2:
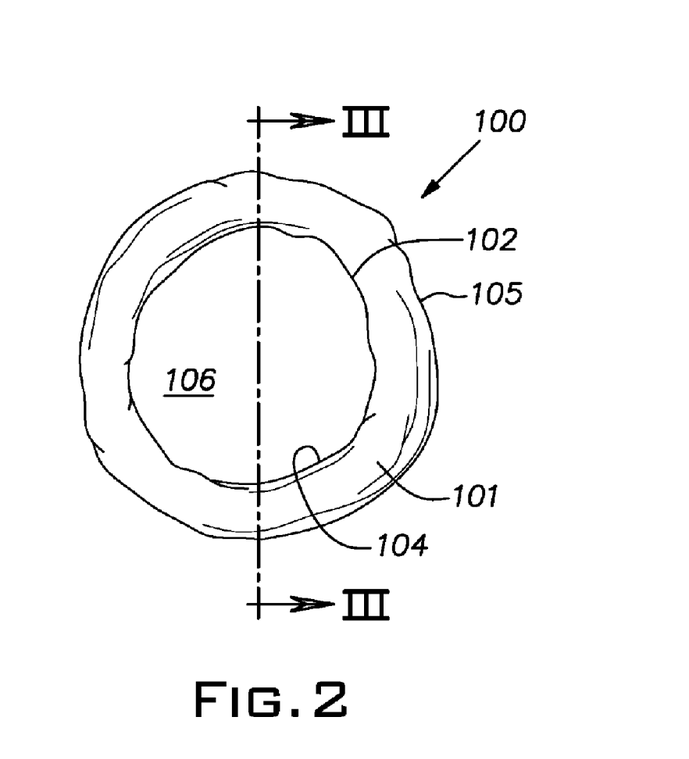
FIG. 2 is an end view of the thermal pack shown in FIG. 1.
Figure 3:
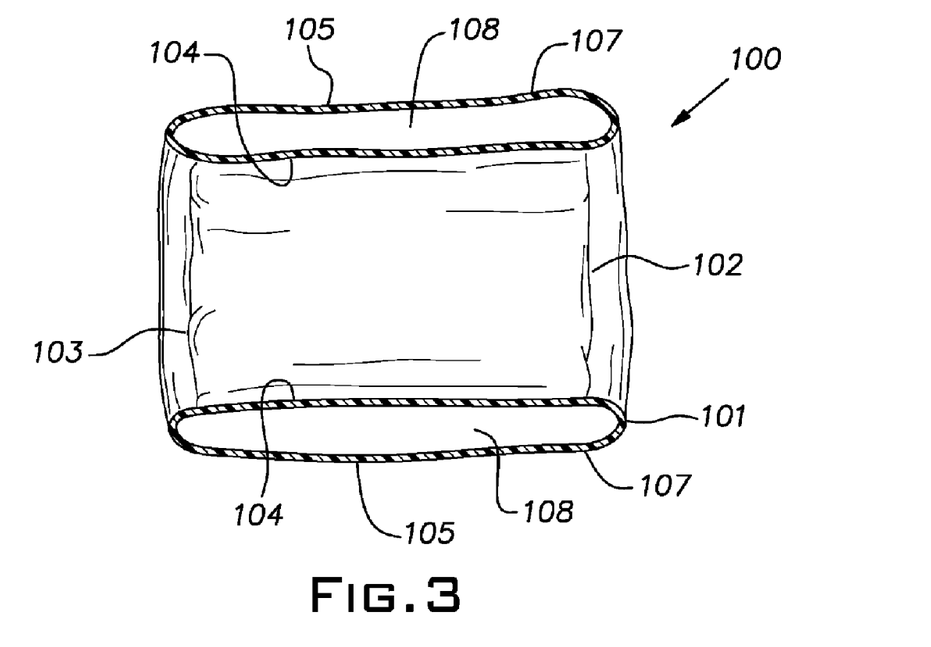
FIG. 3 is a cross-sectional view of the thermal pack taken along the line III-III in FIG. 2.

With reference to FIGS. 1 and 2, a thermal pack 100 according to the invention comprises a tubular body 101 having a first opening 102, a second opening 103, an inner surface 104 and an outer surface 105. The first opening 102, the inner surface 104 and the second opening 103 cooperate to define a passage 106 through the tubular body 101 for a limb. FIG. 3 is a view of the thermal pack 100 as seen along the line III-III in FIG. 2. Thus, a thermal pack in accordance with the invention comprises a tubular body 101 having an elongated generally torus-like shape that is formed of a continuous film of flexible material 107.

The continuous film of flexible material 107 is preferably a polymeric film that remains flexible over a relatively broad temperature range of from about 0° F. to about 130° F. A large number of polymeric films that remain flexible over such a temperature range are known in the art. It will be appreciated that polymeric films used in the invention can be single layer films or multi-layer structures.

Preferably, the continuous film of flexible material exhibits a Shore A durometer hardness of greater than or equal to 85 as measured in accordance with the ASTM 2240.00 standard. More preferably, the continuous film of flexible material exhibits a Shore A durometer hardness of 93±5 as measured in accordance with the ASTM 2240.00 standard. Films possessing such properties are advantageously puncture resistant yet remain flexible.

The continuous film of flexible material preferably has a thickness of from about 3 to about 15 mils. More preferably, the continuous film of flexible material has a thickness of 5±2 mils. It will be appreciated that film thickness is not per se critical, and that a variety of film thicknesses can be used to fabricate a thermal pack in accordance with the invention.

In the presently most preferred embodiment of the invention, the continuous film of flexible material comprises a 5 mil thick copolymer of polyester and polyurethane having a Shore A durometer hardness of about 95 as measured in accordance with the ASTM 2240.00 standard. This film provides several advantages. It can be heat-sealed to itself, which facilitates fabrication of the thermal pack. It does not irritate human skin on contact. And, it remains smooth and flexible over the temperature range of from about 0° F. to about 130° F.

A temperature-retaining fluid 108 is received into the space between the inner surface 104 and the outer surface 105. Throughout the instant specification and in the appended claims, the term "temperature-retaining fluid" means any non-gaseous material that changes shape or direction uniformly in response to an external force imposed upon it and that has the capacity to retain heat or cold for transfer to a limb. The term applies not only to liquids, but also to finely divided solids, gels and combinations of liquids and solid particles having such properties. Preferably, the temperature-retaining fluid is a gel, and more preferably a water-based gel.

Water-based gels can be formulated so as to provide a temperature-retaining fluid that is more viscous than water and does not become a hard solid within the temperature range of from 0° F. and 32° F. Such gels can conform to the contours of the injured limb more comfortably than ice. In addition, such gels tend to retain their desired thermal properties for a longer period of time than water. The gel-filled thermal pack can be pre-heated or pre-chilled, depending upon the type of thermal treatment to be provided. The composition of the gel is not per se critical, but preferably a non-toxic formulation is used to minimize potential injury in the event of exposure.

In another embodiment of the invention, water-filled capsules are dispersed in the temperature-retaining fluid. When the thermal pack is pre-chilled (e.g., through storage in a conventional freezer), the water in the water-filled capsules freezes and becomes solid ice, although the gel remains a viscous fluid. The frozen water-filled capsules extend the period of time during which the thermal pack remains cold. The water-filled capsules are preferably small, such as the size of peas, and substantially spherical, which allows the thermal pack to comfortably conform to limbs.

Other free-flowing solid structures can be dispersed in the temperature-retaining fluid. Examples include inorganic particulates (e.g., sand and/or ceramic particles), spherical structures (e.g., glass and/or metal spheres), magnets and combinations thereof. It will be appreciated that virtually any relatively small substantially free-flowing solid structure can be dispersed in the temperature-retaining fluid, but water-filled capsules are preferably most preferred in view of cost, safety, and effectiveness.

It is often desirable to dispose an insulating layer between the limb and the thermal pack, particularly when the thermal pack has been pre-chilled below the freezing point of water. The insulation layer, which can be formed of fabric or polymeric foam, prevents frostbite. The insulation layer can be wrapped around the limb prior to applying the thermal pack (e.g. a sleeve, a sock or an ACE bandage), or the insulation layer can be disposed as a layer around the tubular body of the thermal pack so as to be coextensive with the inner surface and outer surface of the tubular body.

Figure 4:
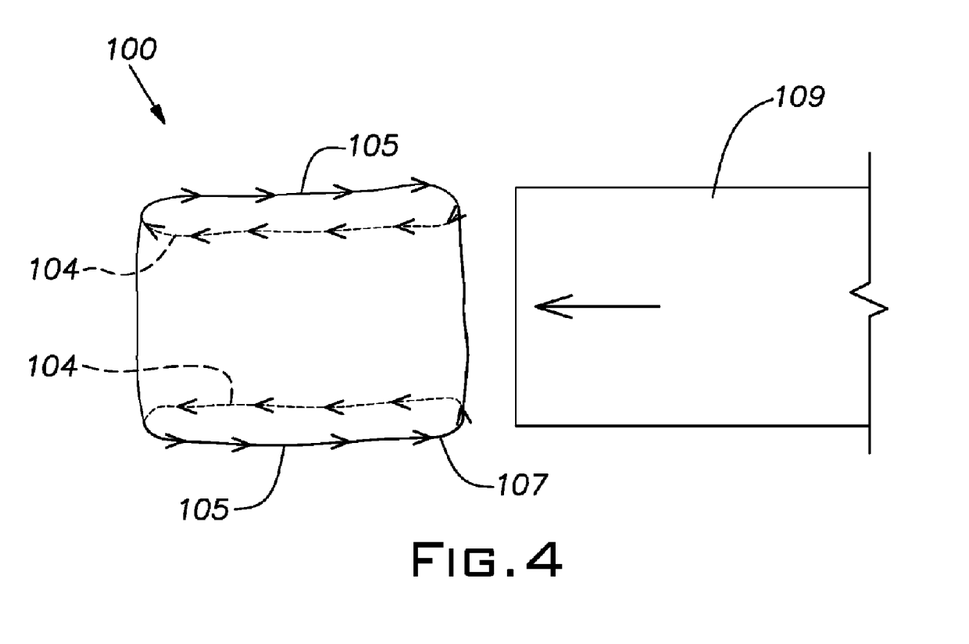
FIG. 4 is a schematic view of an exemplary thermal pack according to the invention about to be rolled onto a limb.

FIG. 4 is a schematic view showing a thermal pack 100 according to the invention as it is about to be placed onto a limb 109. The large arrow shown on the limb 109 shows the direction the limb moves relative to the thermal pack 100. The series of small arrows shown on the inner surface 104 and the outer surface 105 of the thermal pack 100 in FIG. 4 show the movement of the continuous film of flexible material 107 as the thermal pack 100 rolls onto the limb 109. When the diameter of the passage 106 through the tubular body 101 is equal to or smaller than the diameter of the limb 109, the continuous film of flexible material 107 frictionally engages the surface of the limb 109, or an insulating layer disposed between the limb 109 and the continuous film of flexible material 107. Thus, the continuous film of flexible material 107 does not substantially slide relative to the surface of the limb 109, but tubular body defined by the continuous film of flexible material 107 everts as the thermal pack 100 rolls up the limb 109 in the direction opposite the large arrow, retaining its general torus-like shape as it conforms to the contours of the limb. As shown by the series of arrows in FIG. 4, the continuous film of flexible material 107 is eversion-limitless, meaning that the continuous film of flexible material 107 can be everted around the tubular body 101 from the inner surface 104 to the outer surface 105 and back an infinite number of cycles or revolutions in either direction.

Figures 5A, 5B:
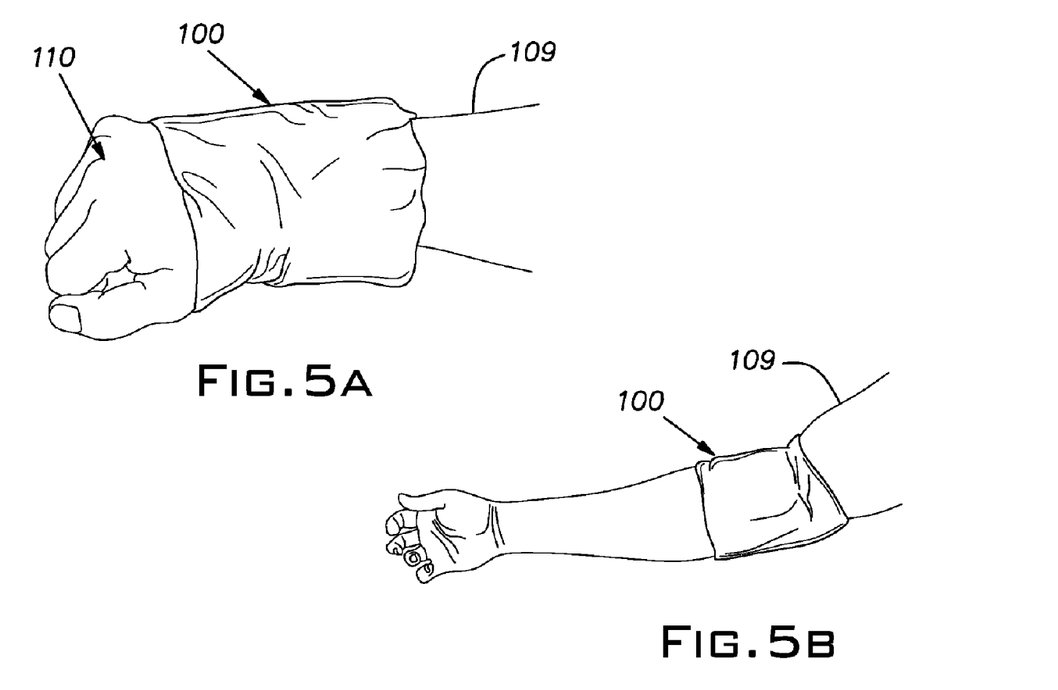
FIG. 5A is a perspective view of an exemplary thermal pack according to the invention positioned on a user's wrist.
FIG. 5B is a perspective view of an exemplary thermal pack according to the invention positioned on a user's elbow.

FIG. 5A shows a perspective view of a thermal pack 100 positioned on a limb 109, which in this illustration is an arm. In this instance, the user first inserted his hand 110 into the passage 106 through the tubular body 101 of the thermal pack 100. The continuous film of flexible material 107 frictionally engaged the user's hand 110, causing the tubular body 101 to roll up the user's hand 110 to the desired location on the limb 109, which in this illustration is the user's wrist. The portion of the continuous film of flexible material 107 that may have initially defined the inner surface 104 of the tubular body 101 when the user's hand 110 was first inserted into the passage 106 through the tubular body 101 everted around the tubular body 101 as the tubular body 101 rolled onto the limb, and may now define the outer surface 105 of the tubular body. The continuous film of flexible material 107 can evert around the tubular body 101 as may times or cycles as is necessary to position the thermal pack 100 as desired. Once positioned as illustrated in FIG. 5A, the thermal pack 100 thus provides circumferential thermal treatment and comfortable compression to the user's wrist.

It will be appreciated that the thermal pack according to the invention can be formed with passages having various configurations depending upon the intended use. In order to insure that the proper compressive force is applied to the limb, it is important that the thermal pack be properly sized. Larger sized thermal packs can be used on legs, and smaller sized thermal packs can be used on arms and children. Thermal packs according to the invention can be custom-sized to provide thermal treatment to human hands, fingers, wrists, elbows, forearms, upper arms, feet, ankles, calves, knees, and thighs. A thermal pack having a longitudinal length of about 4.0 inches and an inner diameter of about 1.0 inch is particularly suitable for use in providing thermal treatment to a human finger. In addition, thermal packs according to the invention can be custom-sized to provide thermal treatment to the limbs and/or bodies of non-human animals, such as dogs, cats, horses and snakes.

When configured for use on a human wrist, the passage through the tubular body is preferably substantially cylindrical in shape with an inner diameter within the range of from about 2.5 to about 4.0 inches. The passage through the tubular body preferably has a length of from about 4.0 to about 6.0 inches. Approximately 16 ounces of water-based gel material is disposed into the space between the inner surface and the outer surface, which results in a gel layer that is about 0.5 inches thick around the entire wrist when the thermal pack is positioned on the user's wrist.

Figure 5C:
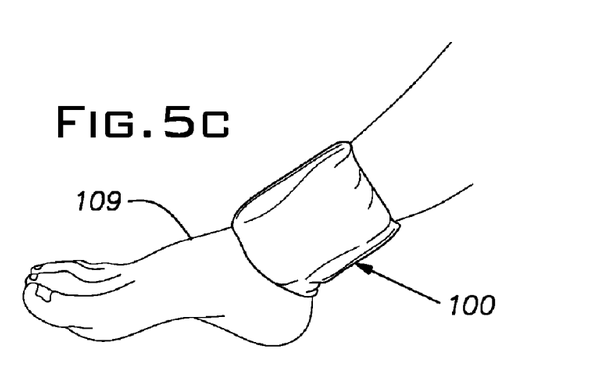
FIG. 5C is a perspective view of an exemplary thermal pack according to the invention positioned on a user's ankle.
Figure 5D:
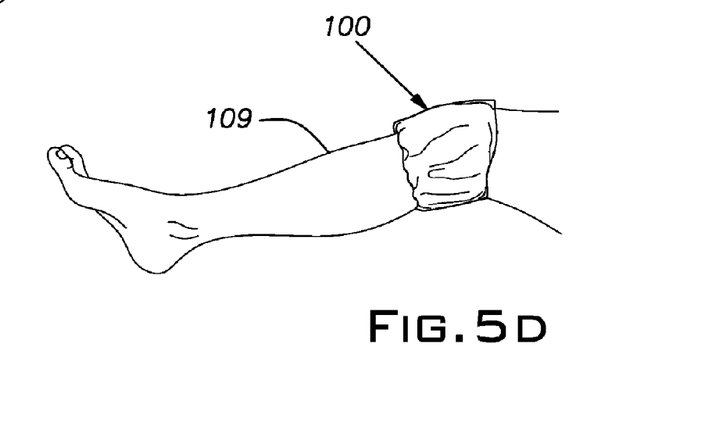
FIG. 5D is a perspective view of an exemplary thermal pack according to the invention positioned on a user's knee.

Thermal packs configured for use on an elbow generally have a passage through the tubular body that is larger in diameter and greater in length than a thermal pack configured for use on a wrist. Thermal packs configured for use on forearms preferably have a tapered passage. Thermal packs configured for elbows (see FIG. 5B), ankles (see FIG. 5C), knees (see FIG. D), calves, thighs, and other body parts are preferably shaped and sized so as to be comfortable when positioned thereon. It will be appreciated that the size of the passage and the amount of gel disposed into the space between the inner surface and the outer surface can be adjusted to suit a particular end use application.

When a thermal pack such as illustrated in FIG. 1 is positioned on a limb at a joint (e.g., circumferentially covering an elbow or a knee), there is a tendency for the temperature retaining fluid to be distributed unevenly between the inner surface and the outer surface of the tubular body, particularly when the joint is flexed in an angular position. For example, when such a thermal pack is used to treat an injured knee, there will often be very little temperature retaining fluid disposed between the inner surface and the outer surface of the tubular body proximal to the knee cap, and a substantially larger volume or thickness of temperature retaining fluid proximal to the sides of the knee joint. The disparity in the volume of temperature retaining fluid can cause uneven radial thermal treatment to the limb at the joint.

Figures 11, 12, 13:
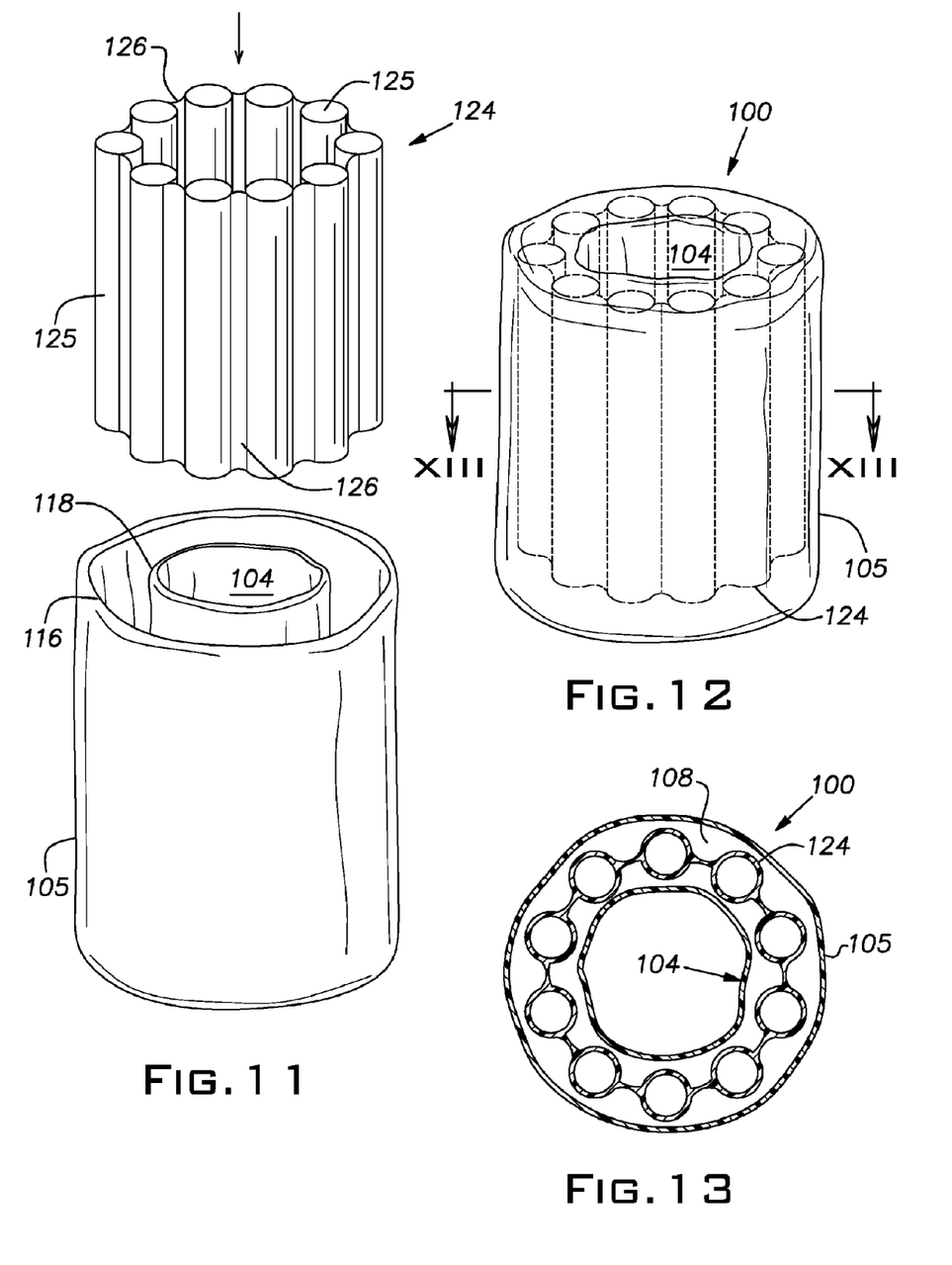
FIG. 11 is a perspective view of an insert and a tube during fabrication of a thermal treatment pack according to the invention.
FIG. 12 is a perspective view of a thermal pack having the insert shown in FIG. 11 disposed between the inner surface and the outer surface of the tubular body.
FIG. 13 is a cross-sectional view of the thermal pack taken along the line XIII-XIII in FIG. 12.

To alleviate this disparity, an insert 124 for inhibiting the displacement of temperature retaining fluid such as shown in FIG. 11 can be disposed between the inner surface and the outer surface of the tubular body. The insert 124 preferably comprises a plurality of sealed tubes 125 that contain a temperature retaining fluid such as a water-based gel. The sealed tubes 125 are themselves sealed together in longitudinal seams 126 (e.g., by heat-sealing) so as to form an insert 124 that comprises a plurality of longitudinally seamed-together sealed tubes 125 that collectively define a cylindrical structure. The sealed tubes 125, individually, can be cylindrical in shape or, more preferably, can have a profile that is similar in cross-section to FLAVOR-ICE brand frozen treats.

In the most preferred embodiment of the invention, the insert 124 is formed of the same material as the continuous film of flexible material 107 used to form the tubular body 101. And, the sealed tubes 125 are filled with the same temperature retaining fluid 108 as is disposed between the inner surface and the outer surface 105 of the tubular body. It will be appreciated, however, that different materials and/or fluids can be used, if desired.

As an alternative to sealed tubes 125, the insert 124 can comprise a cylindrical structure comprising a web of individually sealed pockets that are filled with a temperature retaining fluid. The web may have an open honeycomb-like appearance or, alternatively, may have a closed quilt-like appearance. Because the individual pockets or tubes of temperature retaining fluid are sealed and joined together, the temperature retaining fluid disposed within the individual pockets cannot migrate away in response to flexion of the knee or joint. Thus, a sufficient volume of temperature retaining fluid will remain disposed radially proximal to all portions of the limb at all times regardless of the pressure applied to the individual pockets.

FIGS. 12 and 13 show a perspective view and a cross-sectional view, respectively, of a thermal pack 100 with an insert 124 disposed between an inner surface 104 and an outer surface 105 of the tubular body 101. Temperature retaining fluid 108 fills the space between the inner surface 104 and the outer surface 105 of the tubular body 101, and surrounds the insert 124. Thus, the insert 124 "floats" in the temperature retaining fluid 108 between the inner surface 104 and the outer surface 105 of the tubular body 101. As previously noted, the inner surface 104 and the outer surface 105 of the tubular body 101 are defined by a continuous film of flexible material 107 that can be everted limitlessly around the tubular body 101. The insert 124, however, does not evert. But the continuous film of flexible material 107 everts around the insert 124. Thus, a thermal pack that includes an insert 124 has the same external characteristics in terms of the evertability of its surface as a thermal pack that does not include an insert 124.

It will be appreciated that the insert can be in a form other than a cylindrical structure. For example, donut-shaped inserts can be used to ensure that a sufficient volume of a temperature retaining fluid is disposed proximal to a knee or elbow joint.

One of the advantages provided by the thermal pack according to the invention is the ease by which it can be positioned on an injured limb. Because it is a self-securing device, the thermal pack can be quickly positioned onto an injured limb using only one hand. No fasteners or over-wrap materials are necessary. And once the thermal pack is rolled into the desired position, it tends to remain in the desired position without the need for attachment devices. Thus, for example, a tennis player who injures his or her wrist can roll a pre-chilled thermal pack into place over his or her wrist and then continue to play tennis. Similarly, a person suffering from carpel tunnel syndrome can slip a pre-chilled thermal pack onto his or her wrists and continue to type or perform other routine activities.

Figure 6:
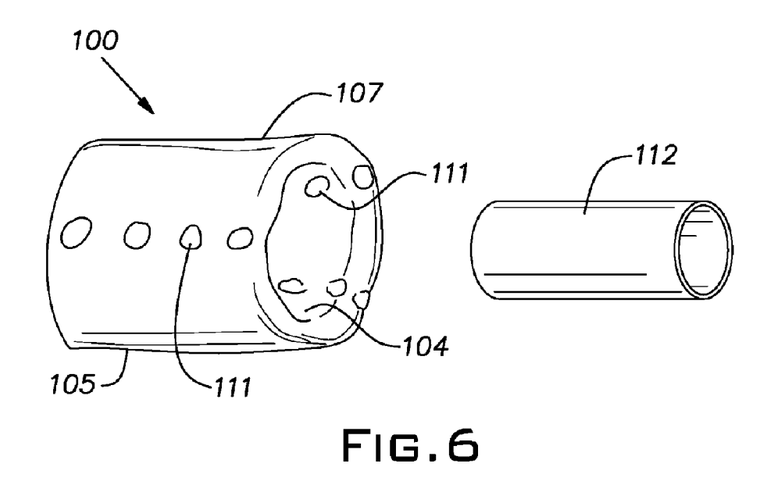
FIG. 6 is a perspective view of another exemplary embodiment of a thermal pack and fabric sleeve according to the invention.

Although it is not necessary in most instances, it is possible to enhance the degree to which a thermal pack remains positioned on a limb by use of hook and loop fastener material such as VELCRO. With reference to FIG. 6, hook material 111 can be affixed to the continuous film of flexible material 107 such that the hook material 111 is disposed on both the inner surface 104 and outer surface 105. An elastic tube or wrapping of loop material 112, such as terry cloth, can then placed around the limb where the thermal pack 100 is to be positioned. Thus, when the thermal pack 100 is positioned in the desired location on the limb, the hook material 111 disposed on the inner surface 104 engages the loop material 112, retaining the thermal pack 100 in the desired position on the limb. The amount and configuration of the hook material 111 disposed on the inner surface 104 is not per se critical. In FIG. 6, the hook material 111 is shown as dots.

Figure 7A:
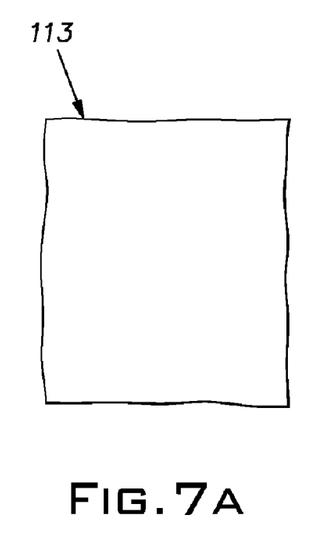
FIG. 7A is a schematic view of a film of flexible material for use in manufacturing a thermal pack according to the invention.
Figure 7B:
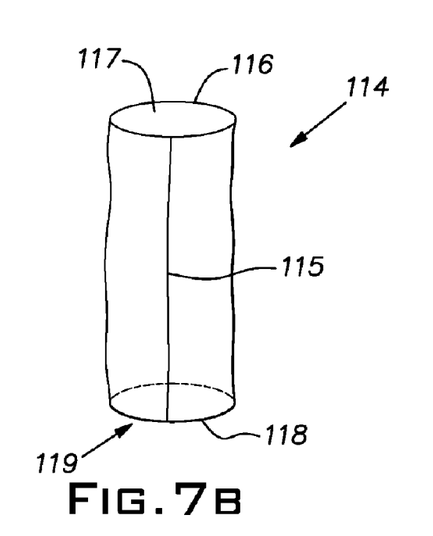
FIG. 7B is a schematic view showing the film in FIG. 7A formed into a tube.

A method of manufacturing a thermal pack is illustrated in FIGS. 7A-7D. With reference to FIG. 7A, a sheet 113 of flexible material such as polyurethane film is cut into a desired shape and size. As shown in FIG. 7B, the sheet 113 is formed into a tube 114 by heat-sealing opposing edges of the sheet together to form a seam 115. Heat sealing can be accomplished using a hot wire sealer or other conventional heat-sealing equipment.

Figure 8A:
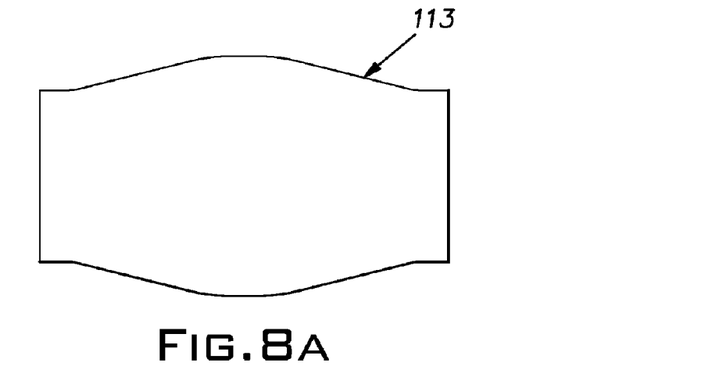
FIG. 8A is a schematic view of a reverse hour glass-shaped sheet of flexible material.
Figure 8B:
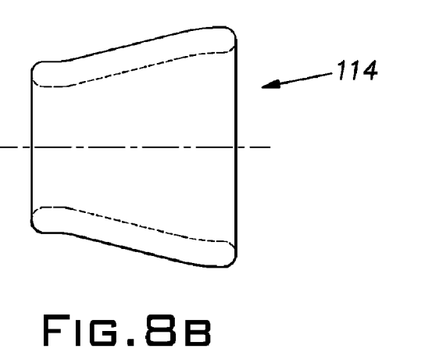
FIG. 8B is a schematic cross-sectional view of a tube formed from the sheet shown in FIG. 8A.
Figure 8C:
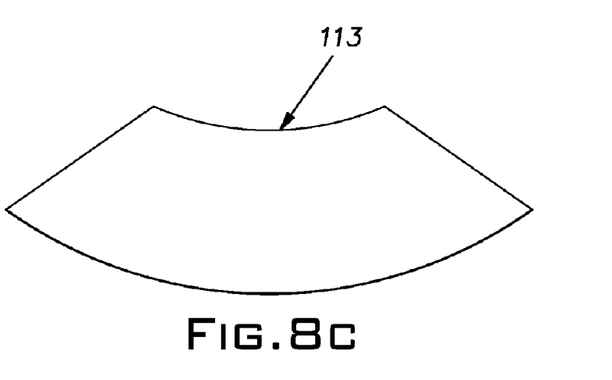
FIG. 8C is a schematic view of an arcuate-shaped sheet of flexible material.
Figure 8D:
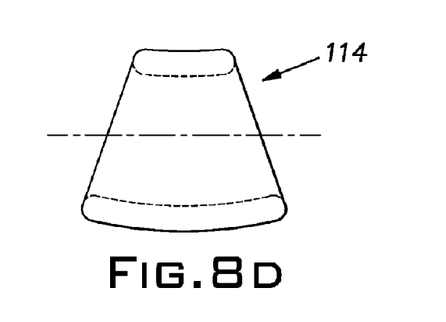
FIG. 8D is a schematic cross-sectional view of a tube formed from the sheet shown in FIG. 8C.

It will be appreciated that a rectangular shaped sheet of film will form a cylindrical tube whereas a reverse hour glass-shaped sheet (see FIG. 8A) will form a flared tube (see FIG. 8B). Similarly, an arcuate-shaped sheet (see FIG. 8C) will form a trapezoidal-like or curved tube (see FIG. 8D). Virtually any sheet shape can be used provided that when the sheet is formed into a tube, the tube has a first edge 116 defining a first open end 117 and an opposing second edge 118 defining a second open end 119, with the open ends being generally of the same size so the first edge 116 and the second edge 118 can be sealed together. Shaped sheets are useful for forming passages that more closely match the contours of the limb onto which the thermal pack is to be placed.

Figure 7C:
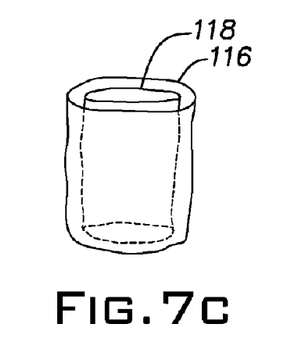
FIG. 7C is a schematic view of the tube in FIG. 7B folded onto itself.

Next, the tube 114 is folded such that the first edge 116 and the second edge 118 are concentric to each other, as shown in FIG. 7C (either the first edge 116 can be outside the second edge 118, or the second edge 118 can be outside the first edge 116). This can be accomplished by turning one of the two open ends of the tube 114 up through the hollow midsection of the tube 114 until the edges are concentric. The two edges are then heat-sealed together using a hot wire or rotary sealing process.

Figure 7D:
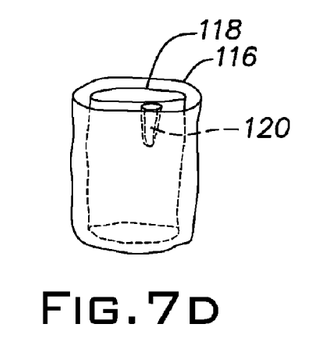
FIG. 7D is a schematic view of the folded tube in FIG. 7C after insertion of a fill valve and sealing.

With reference to FIG. 7D, an optional fill valve 120 is installed between the first edge 116 and the second edge 118 before the two edges are sealed together. The fill valve 120 can be a conventional valve, or can simply constitute a small tube of the flexible material through which the temperature-retaining fluid can be inserted. After filling, the pressure exerted by the temperature-retaining fluid against the continuous film is sufficient to collapse the small tube and prevent the temperature-retaining fluid from leaking. A TEFLON insert is preferably inserted through the fill valve 120 to prevent the valve from being sealed closed when the first edge 116 and second edge 118 are sealed together. Next, the first edge 116 and the second edge 118 are sealed together and around the fill valve 120 using a hot wire or rotary sealing process. The TEFLON insert is then removed from the fill valve 120, and a desired amount of a temperature-retaining fluid is pumped through the fill valve 119 into the space between the inner surface 104 and the outer surface 105 of the tubular body 101. The fill valve 120 can be heat-sealed closed after filling, if desired, but this is usually not necessary.

Preferably, the temperature-retaining fluid is disposed between the inner surface and the outer surface prior to sealing the first edge to the second edge during the manufacturing process. This eliminates the need for a fill valve. It is also possible to form a thermal pack according to the invention without a fill valve by disposing a temperature-retaining fluid in the space between two concentric tubes of flexible material, which are then radially pinch-sealed together at desired intervals to form a tubular body.

Figure 9A:
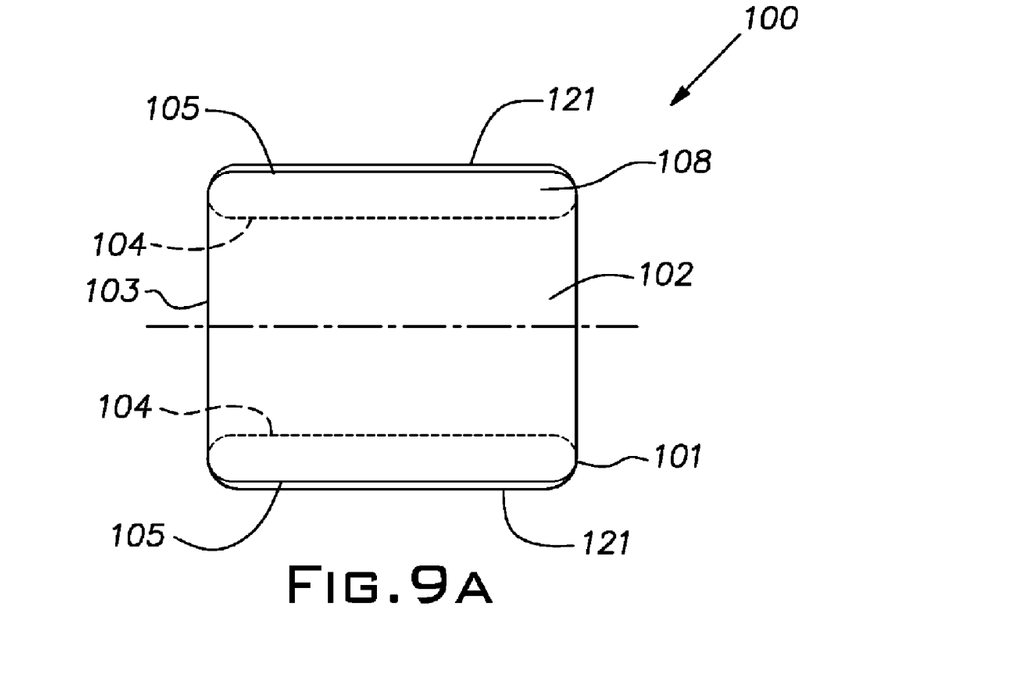
FIG. 9A is a schematic cross-sectional view of an alternative embodiment of a thermal pack according to the invention having an air bladder formed on an outer surface wherein the radial air bladder is in an uninflated state.
Figure 9B:
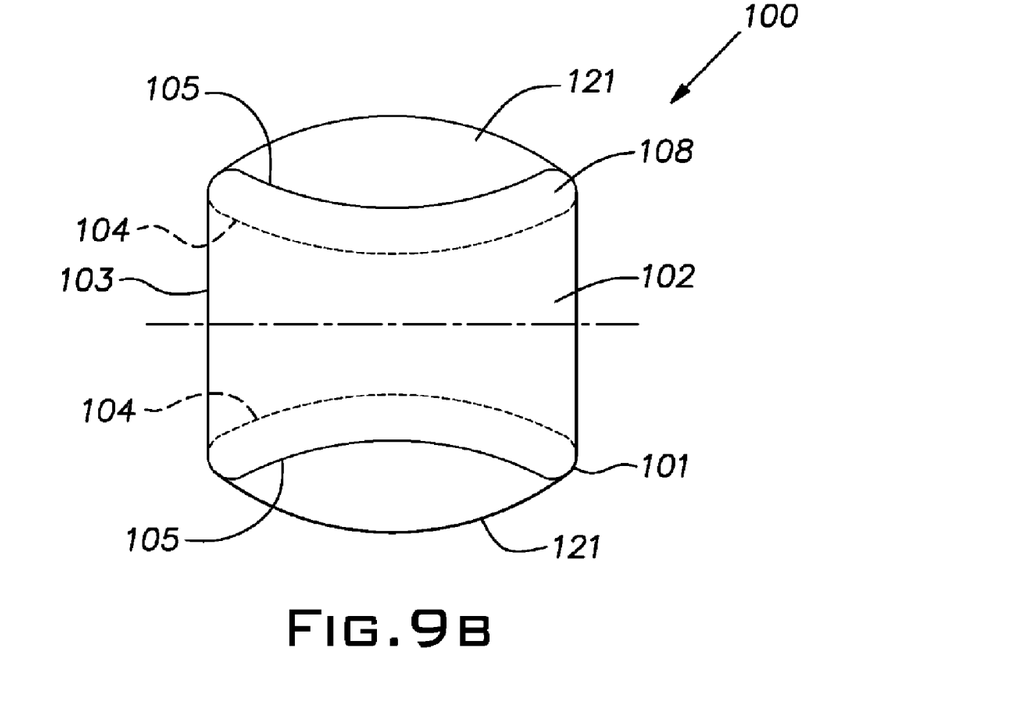
FIG. 9B is a schematic cross-sectional view of an alternative embodiment of a thermal pack according to the invention having an air bladder formed on an outer surface wherein the radial air bladder is in an inflated state.

FIGS. 9A and 9B show cross-sectional views (similar to FIG. 3) of another preferred embodiment of the invention wherein the thermal pack further comprises a selectively pressurizable radial air bladder 121 formed on the outer surface 105 of the tubular body 101. In FIG. 9A, the radial air bladder 121 is in an uninflated state. In FIG. 9B, the radial air bladder 121 is in an inflated state.

The selectively pressurizable radial air bladder 121 is preferably formed by radially heat-sealing a band of flexible film material 129 to the outer surface 105 of the tubular body 101. The band of flexible film material 129 used to form the selectively pressurizable radial air bladder 121 is preferably heat-sealed to the sheet 113 before it is formed into a tube 114, but could likely be sealed to the tube 114 before it is formed into the tubular body 101 or to the outer surface 105 of the tubular body 101 after it is formed. A valve 122, which can be of the same configuration as the optional fill valve 120 for injecting the temperature-retaining fluid into the space between the inner surface and the outer surface or a conventional valve, must be installed to allow for the selective pressurization of the air bladder 121.

Figure 10A:
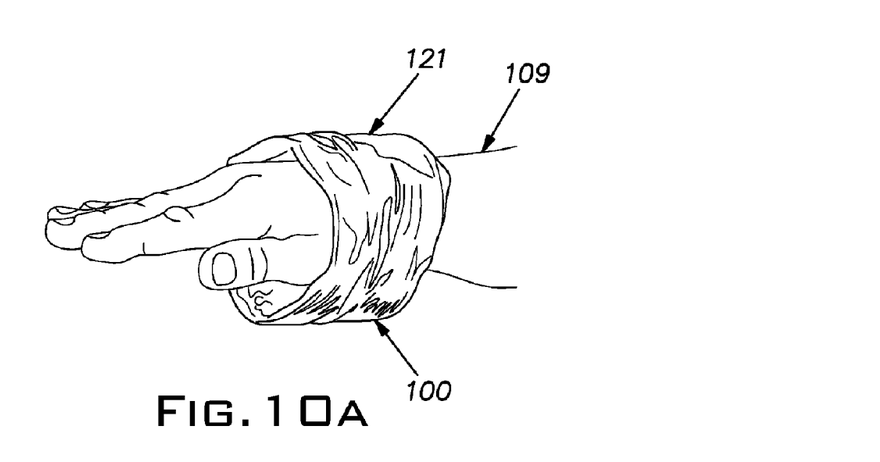
FIG. 10A is a perspective view of an alternative embodiment of a thermal pack according to the invention having an air bladder formed on an outer surface being placed on a user's wrist.

When the thermal pack is provided with a selectively pressurizable radial air bladder, the passage through the tubular body is preferably larger than the user's limb, allowing the thermal pack to be positioned on the user's limb by sliding rather than by rolling. FIG. 10A shows a thermal pack 100 having a radial air bladder 121 as it is being slid onto a user's limb 109, which in FIG. 10A is a wrist. When the thermal pack 100 is properly positioned on the user's limb 109, air is pumped into the radial air bladder 121, which expands the radial air bladder 121 and presses the inner surface 104 of the thermal pack 100 into contact with the user's limb or an insulating layer disposed between the inner surface and the user's limb.

Figure 10B:
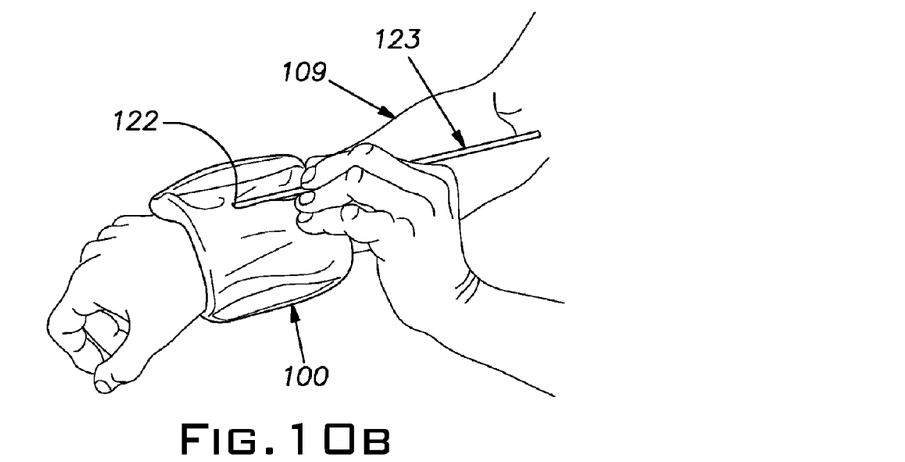
FIG. 10B is a perspective view of the radial air bladder of the thermal pack shown in FIG. 10A being inflated by a user.
Figure 10C:
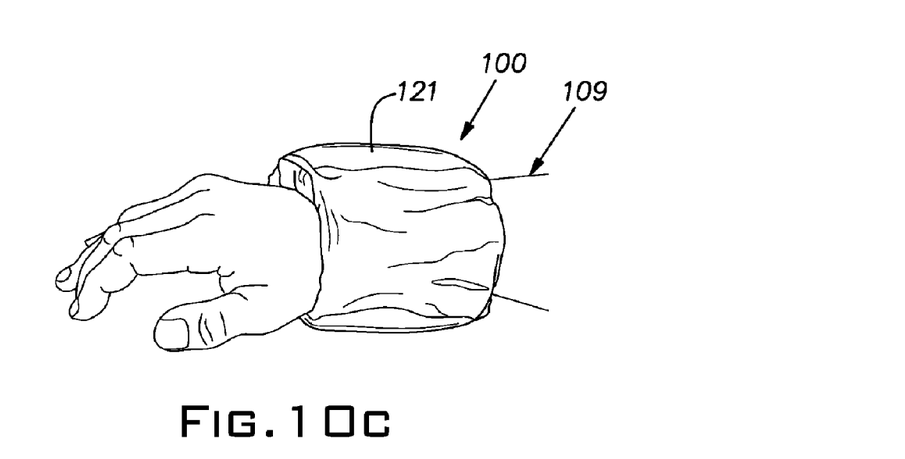
FIG. 10C is a perspective view of the thermal pack shown in FIG. 10A wherein the radial air bladder is in a fully inflated state.

Air can be pumped into the radial air bladder 121 by any means to provide the desired radial compression on the limb. FIG. 10B shows a preferred configuration in which the radial air bladder 121 is selectively pressurized simply by blowing air from one's mouth through a valve 122 into the radial air bladder 121 using flexible tubing 123. The flexible tubing 123 can be reinserted back into the valve 122 to deflate the radial air bladder 121. In FIG. 10C, the radial air bladder 121 of the thermal pack 100 shown in FIG. 10B is shown in a fully inflated state. It will be appreciated that a thermal pack 100 provided with a radial air bladder 121 can include an insert 124 such as described above.

Figure 14:
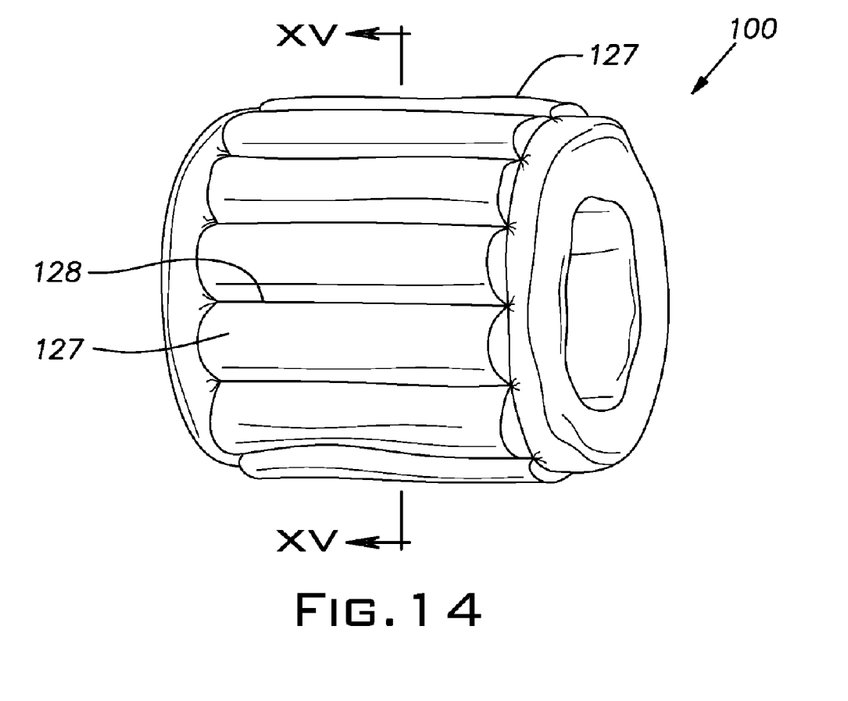
FIG. 14 is a perspective view of yet another alternative embodiment of a thermal pack according to the invention.
Figure 15:
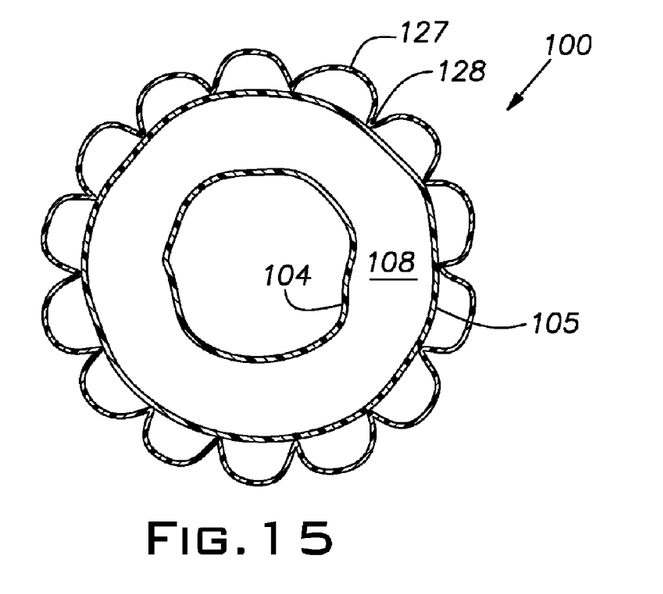
FIG. 15 is a cross-sectional view of the thermal pack taken along the line XV-XV in FIG. 14.

In a preferred embodiment of the invention, portions of the radial air bladder 121 are sealed to the outer surface 105 of the tubular body 101 to form partially-subdivided, interconnected air chambers 127 as shown in FIGS. 14 and 15. The interconnected air chambers 127 can be created by heat-sealing the band of flexible film material 129 to the outer surface 105 of the tubular body 101 to form a plurality of seams 128. Preferably, the seams 128 are longitudinal and relatively evenly spaced apart such that when air is pumped into the radial air bladder 121 to fill the space between the outer surface 105 of the tubular body 101 and the band of flexible film material 129, the seams 128 confine the air to form longitudinal columns that provide longitudinal stability to the thermal pack 100. It will be appreciated, however, that one or more radial (e.g., a series of separated seams resembling dashes that encircle the tubular body), spiral or partially quilted seams cold be used in addition to or alternatively to the longitudinal seams shown in the accompanying figures. Such seams can be used to custom-fit a thermal pack 100 to a particular portion of a limb or joint.

In view of the foregoing, a thermal pack according to the invention provides many advantages. The elongated torus-like shaped tubular body allows the thermal pack to be gently rolled onto a user's limb quickly and easily. Alternatively, the diameter of the passage through the thermal pack is greater than the diameter of the user's limb and the thermal pack is provided with a selectively pressurizable radial air bladder that allows the thermal pack to be slid onto the user's limb quickly and easily. The thermal pack can be placed on an injured limb using one hand, and does not require the use of auxiliary attachment means such as straps or wraps. The thermal pack provides radial compression to the limb, which reduces swelling and speeds up the recovery time. And, the thermal pack provides circumferential thermal treatment to an injured limb.

Thermal packs according to the invention can be pre-chilled in the freezer compartment of a conventional refrigerator. The thermal packs can be used as an ice substitute to keep other items placed in a conventional ice chest or cooler cold, but can be used to treat a sprain or strain. Thus, the thermal packs are particularly suitable for athletic trainers and individuals who participate in sporting events.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A thermal pack comprising a tubular body having a first opening, a second opening, an inner surface and an outer surface, wherein the first opening, the inner surface and the second opening cooperate to define a passage through the tubular body, wherein the inner surface and the outer surface of the tubular body are defined by a continuous eversion-limitless film of flexible material, wherein a water-based gel that does not become a hard solid at 32° F. is received between the inner surface and the outer surface of the tubular body, and wherein a plurality of free-flowing solid structures are dispersed in the gel.

2. The thermal pack according to claim 1 wherein the free-Flowing solid structures dispersed in the gel are selected from the group consisting of water-filled capsules, inorganic particulates, glass spheres, metal spheres, magnets and combinations thereof.

3. The thermal pack according to claim 1 wherein the passage through the tubular body is cylindrical, tapered or flared at the first opening and/or second opening.

4. The thermal pack according to claim 1 wherein the passage through the tubular body has a diameter of 2.5 inches or greater.

5. The thermal pack according to claim 1 wherein the continuous film of flexible material comprises a copolymer of polyester and polyurethane.

6. A thermal pack comprising a tubular body having a first opening, a second opening, an inner surface and an outer surface, wherein the first opening, the inner surface and the second opening cooperate to define a passage through the tubular body, wherein the inner surface and the outer surface of the tubular body are defined by a continuous eversion-limitless film of flexible material, wherein a non-gaseous temperature retaining fluid that does not become a hard solid at 32° F. is received between the inner surface and the outer surface of the tubular body, wherein a selectively pressurizeable radial air bladder is disposed on the outer surface of the tubular body, and wherein the radial air bladder comprises a plurality of partially-subdivided, interconnected air chambers.

7. The thermal pack according to claim 6 wherein the temperature-retaining fluid is a gel.

8. The thermal pack according to claim 7 wherein the gel is water-based.

9. The thermal pack according to claim 7 further comprising a plurality of free-flowing solid structures dispersed in the gel.

10. The thermal pack according to claim 9 wherein the free-Flowing solid structures dispersed in the gel are selected from the group consisting of water-filled capsules, inorganic particulates, glass spheres, metal spheres, magnets and combinations thereof.

11. The thermal pack according to claim 6 wherein the continuous film of flexible material comprises a copolymer of polyester and polyurethane.

12. The thermal pack according to claim 6 wherein the continuous film of flexible material exhibits a Shore A durometer hardness of greater than or equal to 85 as measured in accordance with the ASTM 2240.00 standard.

13. The thermal pack according to claim 6 wherein the continuous film of flexible material has a thickness of from about 3 to about 15 mils.

14. The thermal pack according to claim 6 wherein the partially-subdivided, interconnected air chambers comprise longitudinal columns.

15. A thermal pack comprising a tubular body having a first opening, a second opening, an inner surface and an outer surface, wherein the first opening, the inner surface and the second opening cooperate to define a passage through the tubular body, wherein the inner surface and the outer surface of the tubular body are defined by a continuous eversion-limitless film of flexible material, wherein a non-gaseous temperature retaining fluid that does not become a hard solid at 32° F. and an insert for inhibiting the displacement of temperature retaining fluid are received between the inner surface and the outer surface of the tubular body, wherein the insert comprises a plurality of sealed pockets that are filled with a temperature retaining fluid and are joined together to form a tubular structure.

16. The thermal pack according to claim 15 wherein the sealed pockets comprise individually sealed longitudinal tubes.

* * * * *